United States Patent [19]

Jacobs et al.

[11] Patent Number: 5,274,118

[45] Date of Patent: Dec. 28, 1993

[54] PROCESS FOR PREPARING (2R)-METHYL-4,4,4-TRIFLUOROBUTYLAMINE

[75] Inventors: Robert T. Jacobs, Wilmington, Del.; Andrew G. Brewster; George J. Sependa, both of Macclesfield, England

[73] Assignee: Imperial Chemical Industries PLC, London, England

[21] Appl. No.: 803,291

[22] Filed: Dec. 4, 1991

[30] Foreign Application Priority Data

Dec. 5, 1990 [GB] United Kingdom ............... 9026425

[51] Int. Cl.$^5$ .............................................. C07B 57/00
[52] U.S. Cl. ...................... 548/503; 564/302; 564/303; 564/304; 564/486; 564/488; 564/510; 564/212; 564/366
[58] Field of Search ............... 548/503; 564/303, 302, 564/486, 488, 510, 304

[56] References Cited

U.S. PATENT DOCUMENTS 2,243,977  6/1941  Peyer .................................. 564/486
5,105,014  4/1992  Neumann .......................... 564/486

FOREIGN PATENT DOCUMENTS 0432984  6/1991  European Pat. Off. .

OTHER PUBLICATIONS

March, *Advanced Organic Chemistry*, 3rd Ed., (John Wiley & Sons: New York) 1989, pp. 527–529.
Bernstein et al., *Chem. Abs.* 107: 175881t (1987).
T. Kaneda, "Gas–liquid Chromatographic Separation of Enantiomers as Their Diastereomeric Derivatives, Illustrated with 2-Methylbutyric Acid", *Journal of Chromatography* (1986), 366, 217–224.

Primary Examiner—Glennon H. Hollrah
Assistant Examiner—Scott C. Rand
Attorney, Agent, or Firm—Thomas E. Jackson

[57] ABSTRACT

A process for the preparation of (2R)-methyl-4,4,4-trifluorobutylamine, or an acid addition salt thereof which comprises a) acylating an optically active amine with 2-methyl-4,4,4-trifluorobutanoic acid or a reactive derivative thereof to afford a butyramide;

b) separating (R)-diastereomeric butyramide from (S)-diastereomeric butyramide; and c) converting the (R)-diastereomeric butyramide into the desired (2R)-methyl-4,4,4-trifluorobutylamine, or an acid addition salt thereof. The product may be acylated with a carboxylic acid of formula III

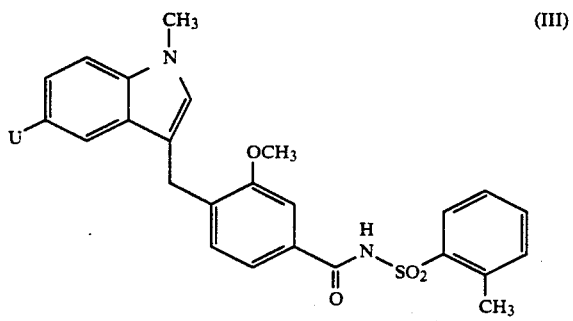

wherein U is carboxy, or a reactive derivative thereof to afford (R)-4-[5-(N-[4,4,4-trifluoro-2-methylbutyl]carbamoyl)-1-methylindol-3-yl-methyl]-3-methoxy-N-o-tolylsulphonylbenzamide. The indole is useful as a leukotriene antagonist, for example in the treatment of asthma or allergic rhinitis.

15 Claims, No Drawings

PROCESS FOR PREPARING (2R)-METHYL-4,4,4-TRIFLUOROBUTYLAMINE

The present invention relates to the preparation of a pharmaceutical intermediate.

European Patent Application Publication Number EP432984, which claims priority from British Patent Application number 8927981.4, filed on Dec. 11, 1989 discloses the compound 4-[5-(N-[4,4,4-trifluoromethyl-butyl]carbamoyl)-1-methylindol-3-ylmethyl]-3-methoxy-N-o-tolylsulphonylbenzamide. This compound has the formula I set out hereinafter. The compound has been found to antagonise the action of one or more of the arachidonic acid metabolites known as leukotrienes. It is useful wherever such antagonism is required, for example in the treatment of those diseases in which leukotrienes are implicated, such as in the treatment of allergic or inflammatory diseases, or of endotoxic or traumatic shock conditions.

The 4,4,4-trifluoro-2-methylbutyl substituent in the compound of formula I has a chiral centre. Thus the compound has (R)- and (S)-forms. The (R)-form is preferred to the (S)-form. Accordingly, the compound of formula (I) is preferably enriched in the (R)-form.

In the following, a compound containing the 4,4,4-trifluoro-2-methylbutyl substituent which is enriched in the (R)- or (S)-form will be identified by the prefix (R)- or (S)-respectively. Where a compound is not identified by such a prefix, it may be in any form.

The compound of formula I enriched in the (R)-form may be prepared by acylating (2R)-methyl-4,4,4-trifluorobutylamine, or an acid addition salt thereof such as the hydrochloride with a carboxylic acid of formula III (formula set out hereinafter) wherein U is carboxy, or a reactive derivative thereof. The acylation is preferably performed in the presence of a dehydrating agent, such as 1-(3-dimethylaminopropyl)-3-ethylcarbodiimide, optionally together with an organic base, for example, 4-dimethylaminopyridine.

A new process has now been found for preparing (2R)-methyl-4,4,4-trifluorobutylamine, or an acid addition salt thereof.

The present invention provides a process for the preparation of (2R)-methyl-4,4,4-trifluorobutylamine, or an acid addition salt thereof, which comprises:

a) acylating an optically active amine with 2-methyl-4,4,4-trifluorobutanoic acid or a reactive derivative thereof to afford a butyramide;

b) separating (R)-diastereomeric butyramide from (S)-diastereomeric butyramide; and c) converting the (R)-diastereomeric butyramide into the desired (2R)-methyl-4,4,4-trifluorobutylamine, or an acid addition salt thereof.

As stated hereinabove, (2R)-methyl-4,4,4-trifluorobutylamine, or an acid addition salt thereof is useful as an intermediate in the preparation of (R)-3-methoxy-4-[1-methyl-5-(2-methyl-4,4,4-trifluorobutylcarbamoyl)indol-3-ylmethyl]-N-(2-methylphenylsulfonyl)benzamide, which is a potent leukotriene antagonist disclosed in European Patent Application Publication Number EP432984.

According to a preferred aspect of the invention, (S)-diastereomeric butyramide obtained in step b) is treated with a strong base, and the resultant butyramide is recycled to step b). The function of the strong base is to catalyse the inversion by racemisation of molecules of the (S)-form of the butyramide into the (R)-form.

Preferably the (S)-diastereomeric butyramide is racemised by the strong base.

It will be appreciated that 2-methyl-4,4,4-trifluorobutanoic acid, being a fluorinated compound, is expensive to obtain. Accordingly, it is highly advantageous to be able to convert both the (R)- and (S)-enantionmers of this compound into the desired (R)-enantiomer of 2-methyl-4,4,4-trifluorobutylamine.

The strong base may be, for example, an alkali metal alkoxide such as sodium or potassium ethoxide or t-butoxide, an alkali metal amide such as lithium isopropylamide, or an alkali metal hydroxide such as sodium hydride.

The optically active amine used in the process according to the invention may be a primary or secondary amine. Examples of optically active amines include alpha-substituted benzylamines, such as alpha-(1–6C)alkyl benzylamines, for instance (S)-phenylethylamine; oxazolidinones, for example (4R,5S)-(+)-4-methyl-5-phenyl-2-oxazolidinone or (4S)-(−)-4-isopropyl-2-oxazolidinone; ephedrine; norephedrine; amino acids and their esters such as proline, proline esters, glutamic acid and valine; glucosamine and 2-amino-1-butanol. Particularly good results have been obtained using an alpha-substituted benzylamine.

The acylation of the optically active amine with 2-methyl-4,4,4-trifluorobutanoic acid may be effected using a conventional method. Thus the optically active amine may be reached with 2-methyl-4,4,4-trifluorobutanoic acid or a reactive derivative thereof, optionally in the presence of a base and/or a dehydrating agent.

A reactive derivative of the acid may be, for example, an acid halide such as the chloride, the anhydride or a mixed anhydride such as that formed with ethanoic acid.

Suitable bases for the acylation include, for example, tertiary amines such as 4-dimethylaminopyridine.

Examples of suitable dehydrating agents include, for example, carbodiimides, for instance dicyclohexylcarbodiimide or 1-(3-dimethylaminopropyl)-3-ethylcarbodiimide, and carbonyldiimidazole.

The acylation is conveniently performed in the presence of a suitable solvent such as an aromatic hydrocarbon, for example, toluene; a halogenated hydrocarbon, for example, dichloromethane; or an ether, for example, tetrahydrofuran or t-butyl methyl ether.

Conveniently, the acylation is effected at a temperature in the range of, for example, from 0° to 120° C., preferably from 15° to 60° C.

In step b) of the process according to the invention, (R)-diastereomeric butyramide may be separated from (S)-diastereomeric butyramide by a conventional physical technique for separating diastereomers, for example by crystallisation or chromatography. Preferably it is separated by crystallisation. Depending upon the particular optically active amine which has been used in step a), and the crystallisation solvent, either (R)- or (S)-diastereomeric butyramide may crystallise out. This may be determined by routine experimentation. Thus the (R)-diastereomeric amide may conveniently be identified by converting both diastereomers into 2-methyl-4,4,4-trifluorobutylamine, and comparing the properties of these amine products with those of an authentic sample of (2R)-methyl-4,4,4-trifluorobutylamine.

Suitable solvents for the crystallisation include, for example, aromatic hydrocarbons such as toluene, saturated hydrocarbons such as petroleum ether, alcohols such as as aqueous industrial methylated spirits, and halogenated hydrocarbons.

It has been found that when an alpha-substituted benzylamine is used as the optically active amine, for example (1S)-phenylethylamine, (R)-diastereomeric butyramide may be separated from (S)-diastereomeric butyramide by crystallisation.

The (R)-diastereomeric butyramide may be converted into the desired (2R)-methyl-4,4,4-trifluorobutylamine or an acid addition salt thereof, by a method known for a conversion of this type.

According to one method, the (R)-diastereomeric butyramide may be hydrolysed, for example by heating with an acid, such as dilute hydrochloric acid, or a weak base to afford (2R)-methyl-4,4,4-trifluorobutanoic acid, which may then be converted into (2R)-methyl-4,4,4-trifluorobutyramide by treatment with ammonia. Alternatively, the (R)-acid may be converted into a reactive derivative thereof, for example the chloride, prior to treatment with ammonia. This amide may then be reduced to afford the desired amine. An advantage of this method is that the optically active amine may be recovered after the hydrolysis.

According to another method an (R)-diastereomeric butyramide which is derived from an oxazolidinone may be reduced, for example with lithium aluminium hydride, to afford (R)-2-methyl-4,4,4-trifluorobutan-1-ol; then this butanol may be reacted with phthalimide to afford an isoindol-1,3(2H)-dione; and then this dione may be reacted with hydrazine monohydrate to afford the desired amine.

According to another method, an (R)-diastereomeric butyramide which is derived from an alpha-substituted benzylamine may be reduced to the corresponding amine, and then hydrogenolysed to afford the desired (2R)-methyl-4,4,4-trifluorobutylamine.

The reduction may conveniently be effected using a hydride reducing agent such as borane, lithium aluminium hydride or sodium borohydride, optionally in the presence of a Lewis acid such as aluminium chloride. Preferably borane is used as the reducing agent.

It has been found that when borane is used, the optical purity of the resultant product is exceptionally high.

The reduction is conveniently effected in the presence of a solvent such as an ether, e.g. tetrahydrofuran, at a temperature in the range of, for example, $-10°$ to $100°$ C., preferably from $0°$ to $80°$ C.

The hydrogenolysis is conveniently effected using a transition metal based hydrogenation catalyst, for example a palladium, platinum or rhodium-based catalyst such as palladium on charcoal. The upper limit for the pressure is not critical. Conveniently the pressure is in the range of from 1 to 10 bar, preferably from 2 to 5 bar. The temperature is conveniently from $0°$ to $120°$ C., preferably $30°$ to $100°$ C.

If desired, the amine product may be converted into an acid addition salt by treatment with an acid, for example hydrochloric acid.

According to another aspect, the invention provides a process for the preparation of (R)-4-[5-(N-[4,4,4-trifluoro-2-methylbutyl]carbamoyl)-1-methylindol-3-ylmethyl]-3-methoxy-N-o-tolylsulphonylbenzamide, which comprises preparing (2R)-methyl-4,4,4-trifluorobutylamine, or an acid addition salt thereof, by a process as described above, and then acylating this with a carboxylic acid of formula III (formula set out hereinafter) wherein U is carboxy, or a reactive derivative thereof.

Thus, for example, an indole carboxylic acid of formula III may be reacted with a suitable dehydrating agent, for example, with 1-(3-dimethylaminopropyl)-3-ethylcarbodiimide, or with a hydrochloride or hydrobromide salt thereof, optionally together with an organic base, for example, 4-dimethylaminopyridine, and with 2-methyl-4,4,4-trifluorobutylamine, or with a salt thereof, especially a hydrochloride or hydrobromide salt, optionally together with an organic base, for example, 4-dimethylaminopyridine, in the presence of a suitable solvent or diluent, for example tetrahydrofuran or 1,2-dimethoxyethane, at a temperature in the range of, for example $10°$ to $85°$ C., for example in tetrahydrofuran at or near $67°$ C.

Alternatively, a reactive derivative of an indole acid of formula III, for example, an acid halide (such as the acid chloride), acid anhydride or mixed acid anhydride (such as that formed with ethyl chloroformate in the presence of an organic base such as, for example triethylamine or 4-dimethylaminopyridine) or a lower alkyl ester (such as the methyl ester) may be used as the acylating agent, conveniently together with a suitable inert solvent or diluent, for example dichloromethane, tetrahydrofuran or 1,2-dimethoxyethane.

The compound of formula III may be prepared as follows:

A compound of formula IV (formula set out hereinafter) wherein U represents $COOR^j$ wherein $R^j$ is a conveniently removed acid protecting group, for example phenyl, benzyl or (1–6C) alkyl optionally bearing an acetoxy, (1–4C) alkoxy or (1–4C) alkylthio substituent, is reacted with a compound of formula V wherein T represents $COOR^h$ wherein $R^h$ is a conveniently removed acid protecting group for example phenyl, benzyl or (1–6C) alkyl optionally bearing an acetoxy, (1–4C) alkoxy or (1–4C) alkylthio substituent to afford a compound of formula VI.

The compound of formula VI may be converted into a corresponding compound of formula VII (formula set out hereinafter) by reaction with a conventional methylating agent, for example methyl iodide.

The compound of formula VII may then be converted into another compound of formula VII in which T represents a carboxy group by selective conversion of the group $COOR^h$, for example by treatment with an alkali metal hydroxide such as lithium hydroxide or sodium hydroxide and water.

The compound of formula VII in which T represents a carboxy group may then be converted into a compound of formula VII in which T represents COCl by reaction into a chlorinating agent, for example thionyl chloride.

The compound of formula VII in which T represents COCl may then be reacted with 2-methylbenzenesulphonamide to afford a compound of formula III in which U is $COOR^j$.

The compound of formula III in which U is $COOR^j$ may then be converted into a compound of formula III in which U is a carboxy group by decomposing the ester group $COOR^j$, for example by treatment with sodium hydroxide and water.

As stated previously, the compound of formula I possesses leukotriene antagonist properties. Thus, it antagonises at least one of the actions of one or more of the arachidonic acid metabolites known as leukotrienes, for example, $C_4$, $D_4$, and/or $E_4$, which are known to be powerful spasmogens (particularly in the lung), to increase vascular permeability and to be implicated in the pathogenesis of asthma and inflammation, as well as of endotoxic shock and traumatic shock. The compound of formula I is thus useful in treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, and psoriasis, as well as vasospastic cardiovascular disease, and endotoxic and traumatic shock conditions.

The compound of formula I is a potent leukotriene antagonist and is useful whenever such activity is desired. For example, the compound of formula I is of value as a pharmacological standard for the development and standardization of new disease models and assays for use in developing new therapeutic agents for treating the diseases in which the leukotrienes are implicated.

When used in the treatment of one or more of the above mentioned diseases, the compound of formula I is generally administered as an appropriate pharmaceutical composition which comprises the compound of formula I as defined hereinbefore together with a pharmaceutically acceptable diluent or carrier, the composition being adapted for the particular route of administration chosen. It may be obtained employing conventional procedures and excipients and binders and may be in a variety of dosage forms. For example, it may be in the form of tablets, capsules, solutions or suspensions for oral administration; in the form of suppositories for rectal administration; in the form of sterile solutions or suspensions for administration by intravenous or intramuscular injection or infusion; in the form of aerosols or nebuliser solutions or suspensions for administration by inhalation; and in the form of powders together with pharmaceutically acceptable inert solid diluents such as lactose for administration by insufflation. If a solid form of a compound of formula I is required, it may be preferred to use an amorphous form, which amorphous form may be prepared by adding an aqueous acid, for example hydrochloric acid, to a solution of the sodium salt of the compound of formula I in an alcohol-water mixture, for example methanol-water mixture, to precipitate the compound of formula I.

For oral administration a tablet or capsule containing up to 250 mg (and typically 5 to 100 mg) of the compound of formula I may conveniently be used. Similarly, for intravenous or intramuscular injection or infusion a sterile solution or suspension containing up to 10% w/w (and typically 0.05 to 5% w/w) of the compound of formula I may conveniently be used.

The dose of the compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received.

The leukotriene antagonist properties of the compound of formula I may be demonstrated using standard test. Thus, for example, they may be demonstrated in vitro using the standard guinea-pig tracheal strip preparation described by Krell (*J. Pharmacol. Exp. Ther.*, 1979, 211, 436) and as also described in European Patent Application publication number 220,066 and in U.S. Pat. No. 4,859,692.

The selectivity of action of compounds as leukotriene antagonists as opposed to non-specific smooth muscle depressants may be shown by carrying out the above in vitro procedure using the non-specific spasmogen barium chloride at a concentration of $1.5 \times 10^{-3}$M, again in the presence of indomethacin at $5 \times 10^{-6}$M.

Alternatively, the antagonistic properties of the compound of formula I can be demonstrated in vitro by a receptor-ligand binding assay described by Aharony (*Fed. Proc.*, 1987, 46, 691).

In general, the compounds of formula I tested demonstrated statistically significant activity as $LTC_4$, $LTD_4$ and/or $LTE_4$ antagonists in one of the above tests at a concentration of about $10^{-8}$M or much less. For example, a pKi value of 9.4 was typically determined for a the compound of formula I substantially in the form of the (R)-enantiomer.

Activity as a leukotriene antagonist may also be demonstrated in vivo in laboratory animals, for example, in a routine guinea-pig aerosol test described by Snyder, et al. (*J. Pharmacol. Methods*, 1988, 19, 219). In this test the particularly useful leukotriene antagonist properties of the carbamoyl derivative of formula I may be demonstrated. According to this procedure, guinea-pigs are pre-dosed with test compound as a solution in poly-(ethylene glycol) (generally 1 hour) before an aerosol challenge of leukotriene $LTD_4$ (starting with 2 ml of a 30 microgram/ml solution) and the effect of the test compound on the average time of leukotriene initiated change in breathing pattern (such as onset of dyspnea) recorded and compared with that in undosed, control guinea-pigs. Percent protection engendered by a test compound was calculated from the time delay to the onset of dyspnea compared to that for control animals. Typically, an $ED_{50}$ of 1.1 mmol/kg for a compound of formula I substantially in the form of the (R)-enantiomer following oral administration was determined, without any indication of untoward side-effects at several multiples of the minimum effective dose. By way of comparison, an oral $ED_{50}$ of 19.2 mmol/kg was measured for the compound of Example 10 of European Patent Application publication number 220,066.

The following non-limiting Examples illustrate the invention.

Notes: NMR data is in the form of delta values, given in parts per million relative to tetramethylsilane as internal standard. Kieselgel is a trade mark of E Merck, Darmstadt, Germany. Yields are for illustration only and are not to be construed as the maximum attainable after conventional process development. Unless otherwise stated, procedures were carried out at ambient temperature and pressure.

EXAMPLE 1 a)

(RS)-4,4,4-trifluoro-2-methyl-N-[(S)-1-phenylethyl]-butyramide

A solution of 2-methyl-4,4,4-trifluorobutanoic acid (10.0 g, 0.064 moles) in dichloromethane (150 ml) was treated with 4-(N,N-dimethylaminopyridine (7.8 g, 0.064 moles) and the mixture was stirred for 15 mins. A solution containing (1S)-phenylethylamine (7.8 g, 0.064 moles) in dichloromethane (50 ml) was added, the mixture was stirred for a further 15 mins, and then a solution of dicyclohexylcarbodiimide (15.9 g, 0.077 moles) in dichloromethane (100 ml) was added. Stirring was continued for 15 hours, then the precipitated dicyclohexylurea was removed by filtration and the filtrate was concentrated to an oil under reduced pressure. The oil was partitioned between aqueous hydrochloric acid (2N, 100 ml) and ether (100 ml) and the two phase mixture was filtered to remove a further quantity of dicyclohexylurea. The layers were separated and the ether fraction was washed sequentially with aqueous hydrochloric acid (2N, 100 ml), aqueous sodium hydroxide solution (2N, 100 ml) and saturated brine (100 ml). The solution was dried over magnesium sulphate, filtered, and concentrated under reduced pressure to an oil, which solidified on standing. The solid, which comprised a mixture of the two diastereomeric butyramides was used directly in the next step.

b)
(R)-4,4,4-trifluoro-2-methyl-N-[(S)-1-phenylethyl]-butyramide

The product of step a) was dissolved in warm toluene (180 ml) and petroleum ether (b.p. 100°-120° C.) (180 ml) was added. The mixture was stirred at room temperature for 15 hours during which time crystallisation occurred. The white crystalline solid was filtered, washed with petroleum ether (b.p. 100°-120° C.) and dried at 60° C. to give impure title compound (4.07 g), contaminated with ca.3% of the unwanted diastereomer, as estimated by HPLC analysis.

The crystallisation mother liquors, which were enriched in the unwanted (S)-diastereomer, were recycled as follows:

The mother liquors (containing ca. 14.0 g of amide mixture) were concentrated under reduced pressure to give an oil, which was redissolved in tetrahydrofuran (150 ml) and treated with potassium tert-butoxide (12.1 g, 2 molar equivalents). The colourless solution became yellow and a slight exotherm was noted. The mixture was stirred for 1 hour, by which time complete equilibration of the diastereomers had occurred, as monitored by HPLC analysis. Water (100 ml) was added, the mixture was stirred for 10 mins, then extracted with ether (2×100 ml). The combined ether extracts were washed with water (2×100 ml) and saturated brine (100 ml) then concentrated to an oil. The oil was dissolved in toluene (130 ml) and petroleum ether (b.p. 100°-120° C.) (130 ml) was added. The solution was seeded with the desired (R)-diastereomeric butyramide and stirred at room temperature for 15 hours. The white crystalline precipitate was filtered, washed with petroleum ether (b.p. 100°-120° C.) and dried at 60° C. to give crude title compound (0.99 g), contaminated with ca.4.0% of the unwanted diastereomer as monitored by HPLC analysis.

The combined crude title compound was recrystallised from petroleum ether (b.p. 100°-120° C.) to give material containing less than 1.0% of the unwanted diastereomer, in ca. 95% recovery, based on combined crude material. NMR (δ, CDCl$_3$): 1.2 (3H,d,J=7 Hz), 1.5 (3H,d,J=7 Hz), 2.0-2.3 (1H,m), 2.4-2.6 (1H,m), 2.6-2.9 (1H,m), 5.0-5.3 (1H,m), 5.6-5.9 (1H,br s) and 7.2-7.5 (5H,m)ppm.

c)
(2R)-Methyl-4,4,4-trifluorobutyl-((1S)-phenylethyl)amine

A solution of borane-tetrahydrofuran complex in tetrahydrofuran (1.0M, 35 ml, 0.035 moles) was cooled to <5° C. under a nitrogen atmosphere and a solution of the product of step b) (3.5 g, 0.0135 moles) in tetrahydrofuran (17.5 ml) was added dropwise over 20 mins, maintaining the temperature below 5° C. throughout. The mixture was then heated to reflux for 3 hours. The mixture was cooled to room temperature and a solution of concentrated hydrochloric acid (5.25 ml) in water (20 ml) was added. The mixture was heated to reflux for 30 mins, then cooled to room temperature and concentrated under reduced pressure to give a damp white solid. The solid was suspended in water (100 ml) and concentrated sodium hydroxide liquor was added to pH12. The mixture was extracted with ether (3×75 ml), the combined organic extracts were dried over magnesium sulphate and the filtered solution was concentrated under reduced pressure to give (2R)-methyl-4,4,4-trifluorobutyl-((1S)-phenylethyl)amine (3.21 g) as a waxy solid. NMR (δ, CDCl$_3$): 1.05 (3H,d,J=7 Hz), 1.35 (3H,d,J=7 Hz), 1.5-2.6 (5H,m), 3.6-3.8 (1H,m) and 7.2-7.5 (5H,m)ppm.

d) (2R)-Methyl-4,4,4-trifluorobutylamine hydrochloride

A solution of the product of step c) (3.21 g, 0.013 moles) in industrial methylated spirit (100 ml) was treated with 10% palladium on carbon (50% water wet paste, 400 mg) and the resulting mixture was hydrogenolysed at 65° C. under a pressure of 3 bar for 3 hours. The mixture was filtered through diatomaceous earth to remove catalyst, concentrated hydrochloric acid (7.5 ml) was added, and the mixture was concentrated under reduced pressure. The residue was dried by azeotropic distillation with toluene (2×75 ml) giving a tan coloured solid (2.07 g).

A sample of the solid (1.75 g) was recrystallised form dichloromethane (13 ml) and ether (13 ml) to give (2R)-methyl-4,4,4-trifluorobutylamine hydrochloride (1.21 g) as a white solid, m.p. 223°-225° C. 19F. NMR (500 MHz, proton decoupled, CFCl$_3$ as reference, 1 mg of title compound and 50 mg of (R)-(−)-2,2,2-trifluoro-1-(9-anthryl)ethanol in CDCl$_3$): −63.86 (s)ppm. NMR shows presence of 3.6% of the (S)-enantiomer at −63.83 (s)ppm.

Preparation of starting materials

1) Ethyl (2E)-2-methyl-4,4,4-trifluorobutenoate

A suspension of (carbethoxyethylidene)triphenylphosphorane (400 g, 1.10 moles) in tetrahydrofuran (600 ml) was treated with aqueous fluoral hydrate (71.5% w/w, 180 g, 1.10 moles) over a period of 4 hours. During the addition the reaction temperature rose to 45° C. and all of the solid dissolved to give a clear brown solution. The mixture was allowed to stand for 15 hours and was then heated under reflux for 3.5 hours. The solution was distilled at 20 mm Hg until the temperature is the distillation flask reaches 140° C. giving ethyl (2E)-2-methyl-4,4-4-trifluorobutenoate as a solution in tetrahydrofuran (Solution (A), 0.751, containing a maximum of 201 g of alkene. NMR(δ, CDCl$_3$): 1.3(3H,t,J=7 Hz), 2.1 (3H,br s), 4.3 (2H,q,J=7 Hz) and 6.7 (1H,m)ppm (plus signals due to tetrahydrofuran).

2) Ethyl 2-methyl-4,4,4-trifluorobutanoate

Solution (A) (0.751) was treated with 10% palladium on carbon (20 g, 50% water wet paste) and the resulting mixture was hydrogenated under a pressure of 2 bar. The reaction was complete after an uptake of hydrogen of 25.91. The catalyst was removed by filtration through kieselguhr to give ethyl 2-methyl-4,4,4-trifluorobutanoate as a solution in tetrahydrofuran (Solution (B), ca. 1l, containing ca. 200 g of ester) which was used directly in the next stage.

3) 2-Methyl-4,4,4-trifluorobutanoic acid

Solution (B) (ca. 1l) was treated sequentially with water (500 ml) and lithium hydroxide monohydrate (150 g, 3.6 moles) and was then heated under reflux (70° C.) for 2 hours. The mixture was allowed to cool to room temperature and the tetrahydrofuran was removed by distillation at 20 mm Hg. The resulting aqueous slurry was treated with concentrated hydrochloric acid to pH2, by which point all solid has dissolved and an oil had separated. The mixture was allowed to stand for 4 days, then the aqueous layer was decanted and extracted with ether (2×200 ml). The separated oil was partitioned between water (500 ml) and ether (500 ml) and the combined ether extracts were dried over magnesium sulphate. Filtration and evaporation under reduced pressure at room temperature gave the crude acid (171.5 g). Distillation of a 45 g sample of crude acid gave 2-methyl- 4,4,4-trifluorobutanoic acid (23.7 g) as a colourless oil, b.p. 173°–176° C. (760 mm Hg), ca. 95% pure by GC analysis. NMR($\delta$ CDCl$_3$): 1.35 (3H,d,J=7 Hz), 2.05-2.30 (1H,m), 2.55-2.95 (2H,m) and 10.2-11.1 (1H, br s)ppm.

EXAMPLE 2

Preparation of
(R)-3-Methoxy-4-[1-methyl-5-(2-methyl-4,4,4-trifluorobutylcarbamoyl)indol-3-ylmethyl]-N-(2-methylphenylsulfonyl)benzamide To a mixture of 4-(5-carboxy-1-methylindol-3-ylmethyl)-3-methoxy-N-(2-methylphenylsulfonyl)benzamide (103.5 g), 4-dimethylaminopyridine (112.4 g), and 1-(3-dimethylaminopropyl)-3-ethylcarbodiimide hydrochloride (51.8 g) in tetrahydrofuran (distilled from sodium benzophenone ketyl) (2.0 l), which had been stirred for 2 hours, was added (R)-2-methyl-4,4,4-trifluorobutylamine hydrochloride (42.6 g); and the reaction mixture was stirred overnight (about 18 hours, incomplete reaction) then heated to reflux for two hours (complete reaction). The cooled reaction mixture was diluted with ethyl acetate (2 l) washed with 1N hydrochloric acid (twice) and brine, dried (MgSO$_4$) and evaporated. The residue (138.6 g) was combined with impure product from similar procedures (28.0 g) and purified by flash chromatography, eluting with methylene chloride:ethyl acetate (sequentially, 1:0, 9:1 and 3:1) to afford a solid which was triturated twice with ether to give the crude title compound (135.2 g) which was recrystallized from ethanol (1.2 l) and acetone (0.3 l) (concentrated by boiling to about 0.9 l and refrigerated) and dried under vacuum to provide the title compound (117.1 g, 65% recovery) as a white crystalline solid; mp 141.5°–143.5° C.; NMR (300 MHz, DMSO-d$_6$): 1.01 (d, 3H, CH$_3$), 2.0–2.2 (m, 2H, CF$_3$CH$_2$), 2.3–2.5 (m, 1H, CHCH$_3$), 2.61 (s, 3H, ArCH$_3$), 3.23 (br t, 2H, CH$_2$N), 3.76 (s, 3H, NCH$_3$), 3.92 (s, 3H, OCH$_3$), 4.07 (s, ArCH$_2$Ar'), 7.13 (s, 1H), 7.17 (d, 2H), 7.38–7.69 (m, 6H), 7.72 (d, 1H), 8.05 (d, 1H), 8.11 (s, 1H), 8.46 (br t, 1H, NHCO); analysis for C$_{31}$H$_{32}$F$_3$N$_3$O$_5$S: calculated: C, 60.48; H, 5.24; N, 6.83%, found: C, 60.47; H, 5.27; N, 6.67%

The starting material 5-carboxyindole derivative may be prepared as follows:

a.
4-(5-Methoxycarbonyl-1-methylindol-3-ylmethyl)-3-methoxybenzoic acid

To a solution of methyl 4-(5-methoxycarbonyl-1-methylindol-3-ylmethyl)-3-methoxybenzoate (105.1 g) in tetrahydrofuran (1.4 l) was added methanol (450 ml) and deionized water (450 ml), followed by an equimolar amount of lithium hydroxide monohydrate (12.00 g). After the reaction mixture had stirred about 20 hours, it was acidified to pH 2 by addition of 6N hydrochloric acid (60 ml). Evaporation of the organic solvents resulted in the precipitation of a crude product (104.2 g) which was filtered and dried under vacuum before it was recrystallized by dissolving it in boiling tetrahydrofuran (600 ml), addition of toluene (about 1.2 l) and concentration to about one liter. Following cooling and stirring overnight, filtration, and drying under vacuum, a first crop is (71.1 g) was obtained. A second, similar recrystallization of this material from tetrahydrofuraN (500 ml) and toluene (1 l) afforded 4-(5-methoxycarbonyl-1-methylindol-3-ylmethyl)-3-methoxybenzoic acid (58.3 g, 57.7%) as an off-white solid; NMR (300 MHz, DMSO-d$_6$): 3.78 (s, 3H, NCH$_3$), 3.83 (s, 3H, CO$_2$CH$_3$), 3.92 (s, 3H, OCH$_3$), 4.07 (s, ArCH$_2$Ar'), 7.17 (d, 1H), 7.18 (s, 1H), 7.43–7.50 (m, 3H), 7.75 (dd, 1H) 8.19 (d, 1H); the same benzoic acid obtained by a similar procedure, but purified by flash chromatography, eluting with (methylene chloride:tetrahydrofuran:acetic acid (sequentially, 1:0:0, 1:9:0, and 0:400:1) followed by isolation and drying under vacuum of crystals formed on standing in methylene chloride:tetrahydrofuran fractions, had mp 228.0°–229.5° C. An additional amount of the benzoic acid (23.6 g, 23.3%), as well as recovered diester (11.5 g, 10.7%), was obtained by concentration and flash chromatography of the mother liquors, eluting with methylene chloride:tetrahydrofuran (sequentially, 1:0, 3:1, 2:1).

b.
4-(5-Methoxycarbonyl-1-methylindol-3-ylmethyl)-3-methoxy-N-(2-methylphenylsulfonyl)benzamide To a solution of 4-(5-methoxycarbonyl-1-methylindol-3-ylmethyl)-3-methoxybenzoic acid (125.9 g) in tetrahydrofuran (3.0 l, distilled from sodium benzophenone ketyl) (prepared by heating at 50° C. until dissolution was complete, followed by cooling to room temperature with an ice-water bath) was added 4-dimethylaminopyridine (56.6 g) and 1-(3-dimethylaminopropyl)-3-ethylcarbodiimide hydrochloride (102.4 g), and the mixture was stirred one hour. To the mixture was added 2-methylbenzene-sulfonamide (67.1 g), and the reaction mixture was stirred about 3 days (for convenience). The reaction mixture was diluted with ethyl acetate (2.0 l) and washed with 1N hydrochloric acid (twice) and brine (3 times, until neutral), and the aqueous extracts were back washed with ethyl acetate. The combined ethyl acetate solution was dried (MgSO$_4$), and partially evaporated to give a slurry of solid in ethyl acetate (about 0.5 l) which was refrigerated overnight. Collection of the solid afforded the crude product (158.5 g, 88%, essentially pure by TlC) as a light pink solid. Recrystallization by dissolution in hot tetrahydrofuran (1.5 l), filtration while hot, dilution with ethyl acetate (2.0 l), and boiling down to a final volume of about 2.5 l afforded a first crop of 4-(5-methoxycarbonyl-1-methylindol-3-ylmethyl)-3-methoxy-N-(2-methylphenylsulfonyl)benzamide (105.5 g, 59%) as a white solid; mp 211°–213° C.; NMR (250 MHz, DMSO-d$_6$): 2.60 (s, 3H, ArCH$_3$), 3.76 (s, 3H, NCH$_3$), 3.82 (s, 3H, CO$_2$CH$_3$), 3.92 (s, 3H, ArOCH$_3$), 4.04 (s, 2H, ArCH$_2$Ar'), 7.15 (d, 1H), 7.22 (s, 1H), 7.38–7.58 (m, 6H), 7.75 (dd, 1H), 8.03 (dd, 1H), 8.17 (d, 1H). (Two additional crops (35.5 g, 20%) and crude product (39.5 g) from concentration of the mother liquors were also obtained.)

c. 4-(5-Carboxy-1-methylindol-3-ylmethyl)-3-methoxy-N-(2-methylphenylsulfonyl)benzamide A mixture of 4-(5-methoxycarbonyl-1-methyl-indol-3-ylmethyl)-3-methoxy-N-(2-methylphenylsulfonyl)-benzamide (130.0 g), tetrahydrofuran (1.0 l) and 1N sodium hydroxide (1.0 l) was heated to about 60° C. overnight, then treated with additional 1N sodium hydroxide (200 ml) and heated an additional 5 hours at 60° C. (likely unnecessary). The cooled reaction mixture was acidified with 6N hydrochloric acid (25 ml) and extracted with ethyl acetate. The ethyl acetate solution was washed with brine (three times), dried (MgSO$_4$) and evaporated to give a solid which was dried at 50° C. under vacuum to give 4-(5-carboxy-1-methylindol-3-ylmethyl)-3-methoxy-N-(2-methylphenyl-sulfonyl)benzamide (12.9 g, 100% when calculated as 0.45 hydrate), mp 255°–257° C.; NMR (300 MHz, DMSO-d$_6$): 2.60 (s, 3H, ArCH$_3$), 3.76 (s, 3H, NCH$_3$), 3.91 (s, 3H, OCH$_3$), 4.05 (s, 2H, ArCH$_2$Ar'), 7.15 (d, 1H), 7.19 (s, 1H), 7.39–7.51 (m, 5H), 7.58 (br t, 1H), 7.72 (dd, 1H), 8.03 (dd, 1H), 8.14 (d, 1H); anaylsis for C$_{26}$H$_{24}$N$_2$O$_6$S.0.45 H$_2$O: calculated: C, 62.37; H, 5.01; N, 5.60%, found: C, 62.60; H, 5.03; N, 5.52%

Methyl 4-(5-methoxycarbonyl-1-methylindol-3-ylmethyl)-3-methoxybenzoate, used in step a., above, may be obtained from methyl indole-5-carboxylate and methyl 4-bromomethyl-3-methoxybenzoate, for example by reaction in the presence of potassium iodide in dimethylformamide, followed by methylation, for example by treatment with sodium hydride in dimethylformamide followed by iodomethane.

EXAMPLE 3 a) (4R,5S)-4-Methyl-3-((2R)-2-methyl-4,4,4-trifluorobutyryl)-5-phenyl-2-oxazolidinone.

To a mixture of (4R,5S)-(+)-4-methyl-5-phenyl-2-oxazolidinone (3.22 g) and tetrahydrofuran (35 ml) at −70° C., under nitrogen was added 1.625M n-butyllithium (12.31 mL) and the mixture was stirred for 15 min. 2-Methyl-4,4,4-trifluorobutyryl chloride (3.5 g) was added to the reaction mixture which was stirred for 15 min at −70° C. and then at 0° C. for 1 hour. The reaction was quenched with ammonium chloride and extracted with ethyl acetate. The organic phase was washed (saturated NaHCO$_3$, brine) and dried (MgSO$_4$). Evaporation and flash chromatography, eluting with 5:95 then 1:9 ethyl acetate:petroelum ether, afforded the two diastereomeric products. Recrystallization from hexane at 20° C. gave (4R,5S)-4-methyl-3-((2R)-2-methyl-4,4,4-trifluorobutyryl)-5-phenyl-2-oxazolidinone (2.376 g, 42%) as colorless needles; mp 72.5°–73.5° C.; TLC, R$_f$=0.43, 1:9 ethyl acetate:petroleum ether; MS(CI): 316 (M+H).

b) (R)-2-Methyl-4,4,4-trifluorobutan-1-ol

Lithium aluminium hydride (10.26 g) was added to a stirred solution of (4R,5S)-4-methyl-3-((2R)-2-methyl-4,4,4-trifluorobutyryl)-5-phenyl-2-oxazolidinone (28 g) in dry diethyl ether (200 mL) at −20° C. under an inert atmosphere, then the mixture was warmed to 0° C. After 2h at 0° C., water (10.27 mL), 10% w/v sodium hydroxide (10.27 mL) and water (31 mL) were added, and the mixture was stirred 20 min. The salts were filtered and washed with distilled diethyl ether. The diethyl ether solution was dried (K$_2$CO$_3$) and diluted with pentane. This resulted in precipitation of recovered (4R,5S)-(+)-4-methyl-5-phenyl-2-oxazolidinone which was isolated by filtration. Concentration of the filtrate by distillation afforded several fractions. The first fractions (bath temperature to 60° C. were pentane and diethyl ether; a second set of fractions (bath temperature 60° C. to 100° C.) was 12 g of a oil that was a 40:60 mixture of (R)-2-methyl-4,4,4-trifluorobutan-1-ol (calculated as 4.8 g alcohol) and diethyl ether by NMR. Warming the remaining tarry residue (bath temperature 85° C.) under vacuum (13,330 Pa) afforded an additional 7.2 g of (R)-2-methyl-4,4,4-trifluorobutan-1-ol (total yield, 12.0 g, 94%); partial NMR (300 MHz, CDCl$_3$-D$_2$O shake); 1.06(d,3H,CH$_3$), 1.41(br t,1H,OH), 1.86–2.07(m,2H,CH(CH$_3$) plus one CF$_3$CH$_2$), 2.31–2.42(m,1H, one CF$_3$CH$_2$), 3.49(dd,1H, one CH$_2$OH), 3.58(dd,1H, one CH$_2$OH).

c) (R)-2-(2-Methyl-4,4,4-trifluorobutyl)-1H-isoindol-1,3(2H)-dione

Diethyl azodicarboxylate (15.4 mL) was added to a 0° C., stirred slurry of (R)-2-methyl-4,4,4-trifluorobutan-1-ol (about 12.0 g), phthalimide (13.4 g), and triphenylphosphine (23.7 g) in diethyl ether (about 6.5 g, see above) and dry tetrahydrofuran (110 mL), warmed to room temperature overnight, and stirred an additional 8 h. The mixture was evaporated, methylene chloride was added to the residue, and the slurry was filtered. The filtrate was purified by flash chromatography, eluting with 1:1 methylene chloride:hexanes, to give (R)-2-(2-methyl-4,4,4-trifluorobutyl)-1H-isoindol-1,3(2H)-dione (17.1 g, 75%) as a white solid; mp 45°–47° C.; partial NMR (400 MHz, CDCl$_3$): 1.08(d,3H,CH$_3$), 1.94–2.07 (m,1H,CF$_3$CH$_2$), 2.14–2.31(m,1H,CF$_3$CH$_2$), 2.36–2.50(m,1H,CHCH$_3$), 3.58(dd,1H,CH$_2$N), 3.64(dd,1H,CH$_2$N).

d) (R)-2-Methyl-4,4,4-trifluorobutylamine hydrochloride

Hydrazine monohydrate (3.1 mL) was added to a stirred solution of (R)-2-(2-methyl-4,4,4-trifluorobutyl)-1H-isoindole-1,3(2H)-dione (17.1 g) in anhydrous ethanol (85 mL) was heated to reflux. After three hours' reflux, the solution was cooled; ethanol (40 mL) was added; and the solution was acidified to pH 1 by addition of concentrated hydrochloric acid and was filtered. The filtrate was evaporated, and the residue was purified by sublimation (bath temperature 170° C., at 6.6 Pa) to yield (R)-2-methyl-4,4,4-trifluorobutylamine hydrochloride as a white solid (9.89 g, 88%); mp 187°–191° C.; partial NMR (300 MHz, DMSO-d$_6$-D$_2$) shake): 1.05 (d,3H,CH$_3$), 2.06–2.36(m,2H,CF$_3$CH$_2$) 2.36–2.54(m,1H,CHCH$_3$) 2.73(dd,1H,CH$_2$N), 2.87(dd,1H,CH$_2$N) 8.20(br s,2H,NH$_2$).

EXAMPLE 4 a) Impure (R)-4,4,4-trifluoro-2-methyl-N-[(S)-1-phenylethyl]-butyramide

Carbonyldiimidazole (22.85 g) was stirred under nitrogen in toluene (80 ml) at ambient temperature. 2-Methyl-4,4,4-trifluorobutanoic acid (20.0 g) was then added dropwise from a dropping funnel, while maintaining the temperature at about 25° C., and the dropping funnel was then washed through with toluene (20 ml). The mixture was then stirred under nitrogen for 1.5 hours. (1S)-Phenylethylamine (15.53 g) was then added dropwise, and the dropping funnel was then washed through with toluene (20 ml). The mixture was then heated to 80° C., and stirring was continued for 1 hour. Hydrochloric acid (2M, 60 ml) was then added, and the mixture was stirred at 80° C. for 15 minutes. The organic layer was then separated and washed with hydrochloric acid (2M, 80 ml), while maintaining the temperature at 80° C. More toluene (175 ml) was then added, and the mixture was concentrated to a volume of 265 ml by distillation at atmospheric pressure. Petroleum ether (b.p. 100°–120° C., 265 ml) was then added, keeping the temperature above 80° C. The mixture was allowed to cool to 42° C., and was then seeded with (R)-4,4,4-trifluoro-2-methyl-N-[(S)-1-phenylethyl]butyramide and then kept at 40° C. for 1 hour. The mixture was then allowed to cool to 30° C., and was stirred at 30° C. overnight. The crystalline product was then filtered and dried at 65° C. to afford (R)-4,4,4-trifluoro-2-methyl-N-[(S)-1-phenylethyl]butyramide (25–29%), contaminated with about 5% of the undesired (S) diastereomer.

b) (R)-4,4,4-trifluoro-2-methyl-N-[(S)-1-phenylethyl]-butyramide

Impure 4,4,4-trifluoro-2-methyl-N-[(S)-1-phenylethyl]butyramide (94(R):6(S)) (5.0 g), prepared by a method similar to that described in step a) above, was dissolved in industrial methylated spirits (18.75 ml) by heating under reflux with stirring. Water (18.75 ml) was then added slowly, while continuing to heat the solution under reflux. The mixture was then heated under reflux for a further 45 minutes, and was then allowed to cool to room temperature, with continued stirring, overnight. The mixture was then filtered, and the crystalline product was washed with water (10 ml) and dried at 65° C. to give the title compound 4.45 g (89%). The product contained only 0.3% of the unwanted (S)-diastereomer.

c) Recovery of (S)-4,4,4-trifluoro-2-methyl-N-[(S)-1-phenylethyl]-butyramide from mother liquors Mother liquors (740 ml, containing at most 30.45 g of 4,4,4-trifluoro-2-methyl-N-[(S)-1-phenylethyl]butyramide) obtained by a procedure similar to that described in step a) above were concentrated to 100 ml by distillation at atmospheric pressure. Petroleum ether (b.p. 100°–120° C.) (100 ml) was then added, and the mixture was allowed to cool to room temperature with stirring overnight. The mixture was then cooled to between 0° and 5° C. for three hours and was then filtered. The crystalline product was then washed with petroleum ether (b.p. 100°–120° C.) (30 ml, twice) and dried at 65° C. to afford 24.8 g (81.4%) of 4,4,4-trifluoro-2-methyl-N-[(S)-1-phenylethyl]butyramide. The ratio of (S) to (R) diastereomer in the product was 2:1.

d) Epimerisation of recovered (S)-4,4,4-trifluoro-2-methyl-N-[(S)-1-phenylethyl]-butyramide 10 g of 4,4,4-trifluoro-2-methyl-N-[(S)-1-phenylethyl]butyramide (diastereomer ratio 2(S):1(R), prepared by a method similar to that described in step c)above) was dissolved in tetrahydrofuran (25 ml) with stirring. Potassium t-butoxide (2.02 g) was then added, together with tetrahydrofuran (5 ml). The resultant solution was then stirred for one hour, by which time complete equilibration of the diastereomers had occured, as monitored by HPLC analysis. Water was then added with cooling to maintain the temperature at 20°–25° C. The solution was then stirred for 10 minutes, and then toluene (25 ml) was added, and the stirring was continued for a further 15 minutes. The organic layer was then separated, washed with water (12.5 ml) and concentrated by distillation at atmospheric pressure to a temperature of 110° C. The volume was adjusted to 80 ml by adding toluene, and the mixture heated under reflux. Petroleum ether (b.p. 100°–120° C.) (80 ml) was then added. The solution was then allowed to cool to 40° C., seeded with (R)-4,4,4-trifluoro-2-methyl-N-[(S)-1-phenylethyl]butyramide and held at 40° C. for 2 hours. The mixture was then allowed to cool to 30° C., and was stirred overnight. The crystalline product was then filtered off, washed with petroleum ether (b.p. 100°–120° C.) and dried at 65° C. to afford 3.20 g (32%) of (R)-4,4,4-trifluoro-2-methyl-N-[(S)-1-phenylethyl]-butyramide contaminated with about 6% of the undesired (S) diastereomer.

FORMULAE

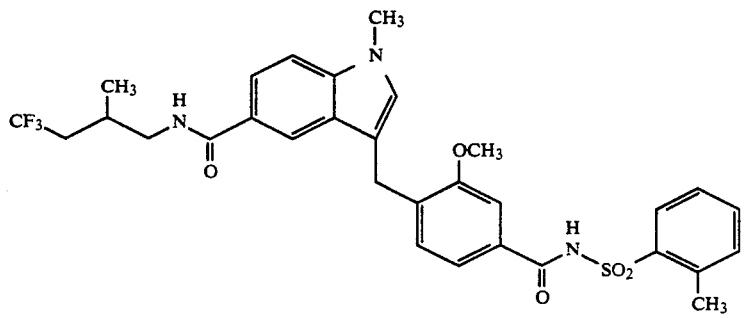

I

FORMULAE

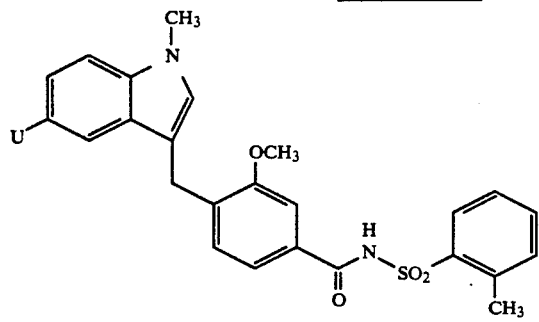
III

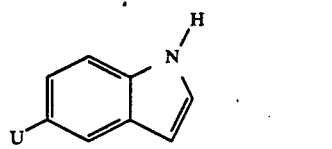
IV

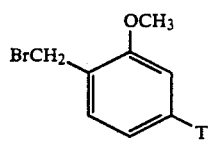
V

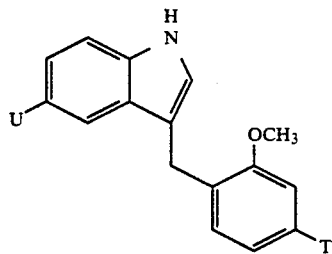
VI

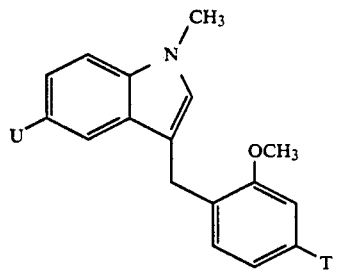
VII

What we claim is:

1. A process for the preparation of (2R)-methyl-4,4,4-trifluorobutylamine, or an acid addition salt thereof, which comprises:
   a) acylating an optically active amine, which optically active amine is an alpha-substituted benzylamine, with 2-methyl-4,4,4 trifluorobutanoic acid or a reactive derivative thereof to afford a butyramide;
   b) separating (R)-diastereomeric butyramide from (S)-diastereomeric butyramide; and
   c) converting the (R)-diastereomeric butyramide into the desired (2R)-methyl-4,4,4-trifluorobutylamine, or an acid addition salt thereof, by reduction to the corresponding amine, and then hydrogenolysis to afford (2R)-methyl-4,4,4-trifluorobutylamine.

2. A process as claimed in claim 1, in which (S)-diastereomeric butyramide obtained in step b) is treated with a strong base, and the resultant butyramide is recycled to step b).

3. A process as claimed in claim 2, in which the strong base is an alkali metal alkoxide, an alkali metal amide or an alkali metal hydroxide.

4. A process as claimed in claim 1 in which the (R)-diastereomeric butyramide is separated from the (S)-diastereomeric butyramide by crystallisation.

5. A process as claimed in claim 1, in which the (R)-diastereomeric butyramide is reduced using borane.

6. A process for the preparation of (R)-4-[5-(N-[4,4,4-trifluoro-2-methylbutyl]carbamoyl)-1-methylindol-3-ylmethyl]-3-methoxy-N-o-tolylsulphonylbenzamide, which comprises:
   a) acylating an optically active amine, which optically active amine is an alpha-substituted benzylamine, with 2-methyl-4,4,4-trifluorobutanoic acid or a reactive derivative thereof to afford a butyramide;

b) separating (R)-diastereomeric butyramide from (S)-diastereomeric butyramide;

c) converting the (R)-diastereomeric butyramide into (2R)-methyl-4,4,4-trifluorobutylamine, or an acid addition salt thereof, by reduction to the corresponding amine, and then hydrogenolysis to afford (2R)-methyl-4,4,4-trifluorobutylamine; and d) acylating the (2R)-methyl-4,4,4-trifluorobutylamine, or an acid addition salt thereof, with a carboxylic acid of formula III:

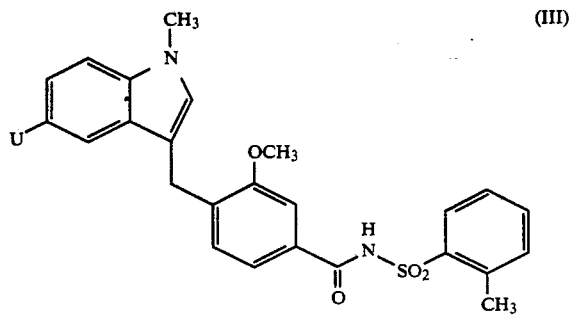

(III)

wherein U is carboxy, or a reactive derivative thereof.

7. A process as claimed in claim 2, in which the (R)-diastereomeric butyramide is separated from the (S)-diastereomeric butyramide by crystallisation.

8. A process as claimed in claim 3, in which the (R)-diastereomeric butyramide is separated from the (S)-diastereomeric butyramide by crystallisation.

9. A process as claimed in claim 2, in which the (R)-diastereomeric butyramide is reduced using borane.

10. A process as claimed in claim 3, in which the (R)-diastereomeric butyramide is reduced using borane.

11. A process as claimed in claim 4, in which the (R)-diastereomeric butyramide is reduced using borane.

12. A process as claimed in claim 7, in which the (R)-diastereomeric butyramide is reduced using borane.

13. A process as claimed in claim 8, in which the (R)-diastereomeric butyramide is reduced using borane.

14. A process as claimed in any one of claims 1–13 in which the alpha-substituted benzylamine is an alpha-(1-6)alkyl benzylamine.

15. A process as claimed in any one of claims 1–13 in which the alpha-substituted benzylamine is (1S)-phenylethylamine.

* * * * *